US010919832B2

(12) United States Patent
Ma et al.

(10) Patent No.: US 10,919,832 B2
(45) Date of Patent: Feb. 16, 2021

(54) METHOD FOR PREPARING LOW-GRADE UNSATURATED FATTY ACID ESTER

(71) Applicant: Dalian Institute of Chemical Physics, Chinese Academy of Sciences, Dalian (CN)

(72) Inventors: Zhanling Ma, Dalian (CN); Wenliang Zhu, Dalian (CN); Xiangang Ma, Dalian (CN); Hongchao Liu, Dalian (CN); Yong Liu, Dalian (CN); Youming Ni, Dalian (CN); Shiping Liu, Dalian (CN); Qiwei Chen, Dalian (CN); Zhongmin Liu, Dalian (CN)

(73) Assignee: Dalian Institute of Chemical Physics, Chinese Academy of Sciences, Dalian (CN)

( * ) Notice: Subject to any disclaimer, the term of this patent is extended or adjusted under 35 U.S.C. 154(b) by 0 days.

(21) Appl. No.: 16/461,120

(22) PCT Filed: Nov. 25, 2016

(86) PCT No.: PCT/CN2016/107246
§ 371 (c)(1),
(2) Date: May 15, 2019

(87) PCT Pub. No.: WO2018/094687
PCT Pub. Date: May 31, 2018

(65) Prior Publication Data
US 2020/0062686 A1  Feb. 27, 2020

(51) Int. Cl.
*C07C 51/353* (2006.01)
*C07C 67/333* (2006.01)
*C07C 67/343* (2006.01)
*B01J 29/24* (2006.01)
*B01J 29/46* (2006.01)
*B01J 29/68* (2006.01)
*B01J 29/76* (2006.01)
*B01J 29/85* (2006.01)
*B01J 29/70* (2006.01)
*B01J 29/83* (2006.01)
*B01J 29/18* (2006.01)
*B01J 29/80* (2006.01)
*B01J 29/06* (2006.01)
*B01J 29/08* (2006.01)
*B01J 29/65* (2006.01)
*C07C 69/52* (2006.01)
*C07C 69/54* (2006.01)
*C07C 69/533* (2006.01)
*C07C 57/03* (2006.01)
*C07C 57/04* (2006.01)

(52) U.S. Cl.
CPC .............. *C07C 51/353* (2013.01); *B01J 29/06* (2013.01); *B01J 29/061* (2013.01); *B01J 29/084* (2013.01); *B01J 29/18* (2013.01); *B01J 29/24* (2013.01); *B01J 29/46* (2013.01); *B01J 29/65* (2013.01); *B01J 29/68* (2013.01); *B01J 29/7007* (2013.01); *B01J 29/7038* (2013.01); *B01J 29/7684* (2013.01); *B01J 29/80* (2013.01); *B01J 29/83* (2013.01); *B01J 29/85* (2013.01); *C07C 67/333* (2013.01); *C07C 67/343* (2013.01); *C07C 57/03* (2013.01); *C07C 57/04* (2013.01); *C07C 69/52* (2013.01); *C07C 69/533* (2013.01); *C07C 69/54* (2013.01)

(58) Field of Classification Search
None
See application file for complete search history.

(56) References Cited

U.S. PATENT DOCUMENTS

| 4,447,641 A * | 5/1984 | Hagen | C07C 67/343 554/161 |
| 4,581,471 A * | 4/1986 | Barlow | C07C 51/353 554/162 |
| 5,977,290 A | 11/1999 | Siebenhaar | |
| 2014/0343319 A1 * | 11/2014 | Goebel | C07C 51/353 562/599 |
| 2015/0343431 A1 * | 12/2015 | Parvulescu | B01J 29/7057 562/599 |

(Continued)

FOREIGN PATENT DOCUMENTS

| CN | 105772057 A | 7/2016 |
| JP | 46-16728 A | 5/1971 |

OTHER PUBLICATIONS

Komatsu ("Aldol condensation catalyzed by acidic zeolites" Studies in Surface Science and Catalysis, 142, 2002, p. 667-674) (Year: 2012).*
Wikipedia entry for "dimethoxymethane", downloaded from https://en.wikipedia.org/wiki/Dimethoxymethane on Mar. 1, 2020 (Year: 2020).*
"MFI" entry of the database of zeolite structures, downloaded from https://asia.iza-structure.org/IZA-SC/material_rm.php?STC=MFI on Mar. 2, 2020. (Year: 2020).*
Wikipedia entry for ZSM-5, downloaded from https://en.wikipedia.org/wiki/ZSM-5 on Jul. 22, 2020 (Year: 2020).*
Wu, Hongxia, "International Search Report, International application No. PCT/CN2016/107246", May 15, 2017, State Intellectual Property Office of the P.R. China.

(Continued)

Primary Examiner — Amy C Bonaparte
(74) Attorney, Agent, or Firm — Edwin A. Sisson, Attorney at Law, LLC; Jeffrey J. Banyas

(57) ABSTRACT

Provided is a method for preparing a lower unsaturated fatty acid ester, which comprises carrying out an aldol condensation reaction between dimethoxymethane (DMM) and a lower acid or ester with a molecular formula of $R_1-CH_2-COO-R_2$ on an acidic molecular sieve catalyst in an inert atmosphere to obtain a lower unsaturated fatty acid or ester($CH_2=C(R_1)-COO-R_2$), wherein $R_1$ and $R_2$ are groups each independently selected from the group consisting of H— and $C_1$-$C_4$ saturated alkyl group.

16 Claims, No Drawings

(56) References Cited

U.S. PATENT DOCUMENTS

2015/0344394 A1* 12/2015 Parvulescu ........... C07C 51/353
562/599

OTHER PUBLICATIONS

Vitcha et al., "Vapor Phase Aldol Reaction", Industrial & Engineering Chemistry Product Research and Development, Mar. 31, 1966, pp. 50 to 53, vol. 5, No. 1.
Saha et al., "Alkaline Earth Metal-Based Metal-Organic Framework: Hydrothermal Synthesis, X-Ray Structure and Heterogeneously Catalyzed Claisen-Schmidt Reaction", Dalton Transations, Jul. 3, 2014, pp. 13006-13017, vol. 43, No. 34, only supplementary data provided, no article.
Van Laren, Martijn, Supplementary European Search Report, EPO application No. 16922428, dated Jul. 1 2020, European Patent Office.

* cited by examiner

METHOD FOR PREPARING LOW-GRADE UNSATURATED FATTY ACID ESTER

TECHNICAL FIELD

The present invention relates to a method for preparing lower unsaturated fatty acid esters, and in particular to a method for preparing acrylic acid and methyl acrylate by an aldol condensation reaction of methyl acetate with dimethoxymethane.

BACKGROUND

Acrylic acid and methyl acrylate are important chemical raw materials. They can be used as coatings, flocculants, dispersants and binders, and are widely applied in construction, water treatment, daily chemical, soil treatment and leather industries, being closely related to people's daily life. At present, the most commonly used method for preparing acrylic acid and methyl acrylate in the industry is a process for two-stage oxidation of propylene, that is, propylene is oxidized to acrolein in the first step, and is further oxidized to obtain acrylic acid. However, the raw material of propylene for the method is derived from petroleum, a non-renewable resource, which does not conform to the concept of sustainable development.

The Lucite company in Britain accomplished the industrial production of methacrylic acid and its esters by using aldol condensation reaction for the first time in 2010, with an annual output of 12,000 tons. In the first step of this method, methyl propionate was synthesized from the raw materials of ethylene, carbon monoxide and methanol, etc, and the product was separated to obtain pure methyl propionate; and in the second step, methyl propionate and methanol were passed through a fixed bed reactor loaded with a basic catalyst of cesium oxide, and the product was subsequently subjected to crude separation and rectification to obtain methyl methacrylate. The method fully utilizes the coal-based raw materials of methanol and carbon monoxide, which is in line with China's energy structure of rich-in-coal, poor-in-oil and lean-in-gas, providing a new route for our industrial preparation of acrylic acid and its esters. Acetic acid and methyl acetate are important organic chemical raw materials, which can be obtained by carbonylation of the coal-based raw material of methanol. With the rapid development of C1 chemistry, the overcapacity of acetic acid and methyl acetate has been caused. Acrylic acid and methyl acrylate can be prepared by the aldol condensation reaction of acetic acid and methyl acetate as cheap raw materials with formaldehyde. This provides a feasible route for the sustainable preparation of acrylic acid and methyl acrylate.

An aldol condensation reaction was performed by using acetic acid, propionic acid and formic acid on a silica catalyst loaded with an alkaline earth metal oxide in the patent JP71016728-B in 1967, to prepare the acrylic acid or methacrylic acid product. A Decalsos molecular sieve catalyst loaded with an alkaline earth metal was prepared by James F. Vitcha (I & EC product research and development 1966, 5:50-53) in 1966, which catalyzed the aldol condensation reaction of acetic acid and formaldehyde to prepare acrylic acid and its esters, wherein formaldehyde was supplied from an aqueous solution of formalin. Two kinds of materials loaded with alkaline earth metals, Mg-MOF and Ca-MOF, were prepared by Debraj Saha (Dalton Trans. 2014, 43:13006-13017) in 2014, which could well catalyze the aldol condensation reaction. A series of V—P—O composite catalysts were prepared by Mamoru Ai (Bull. Chem. Soc. Jpn. 1990, 63:1217-1220; Bull. Chem. Soc. Jpn. 1990, 63:3722-3724, etc), which could effectively catalyze the aldol condensation reaction of propionic acid (or propionic ester) or acetic acid (or acetic ester) to prepare lower unsaturated fatty acid esters.

The catalysts used in the aldol condensation reactions studied in the above literatures are mostly basic catalysts or acid-base bifunctional catalysts. The preparation processes generally include using impregnation, ion exchange, coprecipitation and the like to load the active components on the support, which have the disadvantages of being such as cumbersome in preparation, complicated in influence factor, low in reproducibility and easy to lose active ingredients, and cannot meet the needs of industrial large-scale production.

SUMMARY OF THE INVENTION

The object of the present invention is to provide a new method for preparing a lower unsaturated fatty acid ester.

The aldol condensation reaction can be carried out not only under a basic catalyst but also under acidic conditions. A solid acid molecular sieve widely produced in the industry can be used as a catalyst, so as to avoid the problems of difficulty in separation of the product and so on. The solid acid molecular sieve has advantages of such as rich pore structure, simple preparation and wide source, and has good industrial application prospects for catalyzing the aldol condensation reaction.

Based on this, the present invention provides a new method for preparing lower unsaturated fatty acid esters, which comprises carrying out an aldol condensation reaction between dimethoxymethane (DMM) and an acid or ester with a molecular formula of $R_1$—$CH_2$—COO—$R_2$ in a reactor loaded with an acidic molecular sieve catalyst to obtain the corresponding lower unsaturated fatty acid or ester, wherein $R_1$ and $R_2$ are groups each independently selected from the group consisting of H—, $CH_3$—, $CH_3CH_2$—, $CH_3(CH_2)_2$— and $CH_3(CH_2)_3$—, etc.

In a preferred embodiment, the lower unsaturated fatty acid or ester is further hydrogenated to produce the corresponding saturated alcohols.

In a preferred embodiment, $R_1$ and $R_2$ are each selected from H— and $CH_3$—.

In a preferred embodiment, the dimethoxymethane (DMM) and the lower saturated acid ester of $R_1$—$CH_2$—COO—$R_2$ are respectively carried into a reaction tube by a high pressure pump or a saturated gas to come into contact with the acidic molecular sieve catalyst.

In a preferred embodiment, the acidic molecular sieve catalyst comprises any one of a silica-alumina molecular sieve and an aluminum phosphate molecular sieve or a combination thereof; preferably, the topology of the acidic molecular sieve catalyst comprises any one of RHO, CHA, FER, MFI, MOR, FAU and Beta or a combination thereof; more preferably, the acidic molecular sieve catalyst comprises any one of a SAPO-34 molecular sieve, a DNL-6 molecular sieve, a ZSM-35 molecular sieve, a ZSM-5 molecular sieve, a MOR molecular sieve, a Y molecular sieve, a Beta molecular sieve and a MCM-22 molecular sieve or a combination thereof.

In a preferred embodiment, the atomic ratio of silicon to aluminum of the silica-alumina molecular sieve in the acidic molecular sieve catalyst is in a range from 1 to 50, preferably from 2.5 to 25.

In a preferred embodiment, the acidic molecular sieve catalyst further comprises a product modified by an element other than the framework constituent elements of the molecular sieve.

In a preferred embodiment, the acidic molecular sieve catalyst further comprises one or more metal elements selected from the group consisting of potassium, cesium and copper; the metal element is introduced into the acidic molecular sieve catalyst by in-situ synthesis, metal ion exchange or impregnation; the weight percent of the metal element calculated by metal elementary substance is in a range from 0.01 wt % to 10.0 wt %, based on the total weight of the acidic molecular sieve catalyst.

In a preferred embodiment, the acidic molecular sieve catalyst comprises any one selected from the group consisting of alumina, silica, zirconia and magnesia or a combination thereof as a binder; the content of the binder is in a range from 0 wt % to 50 wt %, based on the total weight of the acidic molecular sieve catalyst.

In a preferred embodiment, the molar ratio of dimethoxymethane (DMM) to the lower saturated acid ester in the feed gas is in a range from 1/20 to 5/1, preferably from 1/10 to 2/1.

In a preferred embodiment, the aldol condensation reaction is carried out at a temperature in a range from 200° C. to 400° C. and a pressure in a range from 0.2 MPa to 15.0 MPa, preferably from 250° C. to 350° C. and from 0.2 MPa to 5.0 MPa.

In a preferred embodiment, the total mass space velocity of raw materials is in a range from 0.05 h$^{-1}$ to 10.0 h$^{-1}$, preferably 0.3 h$^{-1}$ to 2.0 h$^{-1}$.

In a preferred embodiment, the aldol condensation reaction is carried out in a fixed bed reactor, a fluidized bed reactor or a tank reactor.

In a preferred embodiment, the aldol condensation reaction is carried out in an atmosphere comprising any one of $N_2$, He, Ar, $CH_4$, $C_2H_6$, $H_2$, CO and $CO_2$ or a combination thereof.

The present invention provides a new method for preparing lower unsaturated fatty acid esters, in particular a new method for preparing acrylic acid and methyl acrylate. The method is carried out on an acidic molecular sieve catalyst and has the advantages of being such as high in reactivity, simple in industrial preparation of catalyst and not easy to lose catalytic active ingredients, and thus has good industrial application prospects.

DETAILED DESCRIPTION OF THE EMBODIMENT

The present invention provides carrying out an aldol condensation reaction between an acid or ester with a molecular formula of $R_1$—$CH_2$—COO—$R_2$ and dimethoxymethane (DMM) in a reactor loaded with an acidic molecular sieve to prepare a lower unsaturated fatty acid or ester ($CH_2$=$C(R_1)$—COO—$R_2$), wherein $R_1$ and $R_2$ are groups each independently selected from the group consisting of H—, $CH_3$—, $CH_3CH_2$—, $CH_3(CH_2)_2$— and $CH_3(CH_2)_3$—, etc.

In a specific embodiment, the present invention provides a method for preparing acrylic acid and its esters by an aldol condensation of methyl acetate and dimethoxymethane on an acidic molecular sieve catalyst.

Preferably, the silica-alumina molecular sieve in the acidic molecular sieve catalyst used in the present invention has an atomic ratio of silicon to aluminum in a range from 1 to 50, more preferably from 2.5 to 25.

Preferably, the acidic molecular sieve catalyst further comprises one or more metal elements selected from the group consisting of potassium, cesium and copper; the metal element is introduced into the acidic molecular sieve catalyst by in-situ synthesis, metal ion exchange or impregnation; preferably, the weight percent of the metal element calculated by metal elementary substance is 0.01 wt % to 10.0 wt %, based on the total weight of the acidic molecular sieve catalyst.

Preferably, the acidic molecular sieve catalyst used in the present invention comprises any one selected from the group consisting of alumina, silica, zirconia and magnesia or a combination thereof as a binder; preferably, the content of the binder is in a range from 0 wt % to 50 wt %, based on the total weight of the acidic molecular sieve catalyst.

Preferably, the lower fatty acid ester used in the present invention is methyl acetate, and acrylic acid and methyl acrylate are obtained after the aldol condensation reaction.

Preferably, the aldol condensation reaction used in the present invention is carried out under the following conditions: a temperature in a range from 200° C. to 400° C.; a reaction pressure in a range from 0.2 MPa to 5.0 MPa; a total mass space velocity of raw materials in a range from 0.3 h$^{-1}$ to 2.0 h$^{-1}$.

Preferably, the aldol condensation reactor used in the present invention is a fixed bed reactor, a fluidized bed reactor or a tank reactor.

Preferably, the aldol condensation reaction is carried out in an atmosphere comprising any one of $N_2$, He, Ar, $CH_4$, $C_2H_6$, $H_2$, CO and $CO_2$ or a combination thereof.

Furthermore, although it is not particularly limited, in a preferred aldol condensation reaction, the molar ratio of dimethoxymethane to methyl acetate is in a range from 1/10 to 2/1.

EXAMPLES

The present invention is described in detail below by means of examples, but the present invention is not limited to these examples.

The aluminum phosphate molecular sieves DNL-6 and SAPO-34 were produced and supplied by the Dalian Institute of Chemical Physics according to the methods reported in Microporous and Mesoporous Materials 144 (2011) 113-119 and Microporous and Mesoporous Materials 111 (2008) 143-149, respectively; the remaining molecular sieves and the related raw materials were purchased commercially.

The analytical methods and conditions in the examples of the present application are as follows:

The raw materials and products were tested online by Agilent's Aligent 7890A gas chromatograph using Agilent's FFAP capillary column.

According to an embodiment of the present application, a fixed bed reactor was used, the total mass space velocity of the raw materials was in a range from 0.3 h$^{-1}$ to 2.0 h$^{-1}$, the reaction temperature was in a range from 200° C. to 400° C., and the reaction pressure was in a range from 0.2 MPa to 5.0 MPa. The raw materials entered the reactor in the following way:

The raw materials of methyl acetate and dimethoxymethane were thermostated in a water bath (20° C.) and bubbled through nitrogen $N_2$, the saturated steam carrying the raw materials entered the fixed bed reactor, and the amount of substance of the raw materials entering the reactor might be adjusted according to the flow rate of nitrogen. The saturated vapor pressure of the raw materials under different temperature conditions can be calculated by the following formula:

$$lgP^* = A - B/(t+C)$$

Among them, A, B and C represent respectively the physical property parameters of different raw materials, which can be found in the Lange's Handbook of Chemistry, and t represents temperature. This allows the calculation for the saturated vapor pressure of the raw materials at any temperature. The amount of substance of the raw materials entering the reactor per unit time can be calculated by the saturated vapor pressure.

The conversion rate of dimethoxymethane=[(the molar number of dimethoxymethane in the feed)−(the molar number of dimethoxymethane in the discharge)]÷(the molar number of dimethoxymethane in the feed)×(100%)

The conversion rate of methyl acetate=[(the molar number of methyl acetate in the feed)−(the molar number of methyl acetate in the discharge)]÷(the molar number of methyl acetate in the feed)×(100%)

The selectivity of acrylic acid and methyl acrylate= (the molar number of carbon in acrylic acid and methyl acrylate in the discharge)÷(the total molar number of carbon in all products—the molar number of carbon in dimethyl ether)× (100%)

The products in the examples of the present application contain a large amount of dimethyl ether, which might be recycled in industry to replenish raw materials, and therefore, the dimethyl ether product was not considered in calculating the selectivity.

1 Preparation Example of Catalyst

1.1 Aluminum Phosphate Molecular Sieve

SAPO-34 and DNL-6 were prepared by the Dalian Institute of Chemical Physics in accordance with the hydrothermal method. The raw powders were calcined at 550° C. for 4 hours, and extruded to obtain 1 # and 2 # catalysts of 20-40 mesh for use, respectively.

1.2 Silica-Alumina Molecular Sieve 100 g of Na—Y, Na-MOR, Beta and Na-ZSM-5 molecular sieves after calcination, with an atomic ratio of silicon to aluminum of 2.5, 6.5, 20 and 21.5 respectively, were exchanged three times with 0.5 mol/L aqueous ammonium nitrate solution respectively (2 hours for each time), washed with deionized water, dried, and calcined at 550° C. for 4 hours to obtain a hydrogen type Y molecular sieve, a hydrogen type MOR molecular sieve, a hydrogen type Beta molecular sieve and a hydrogen type ZSM-5 molecular sieve, which were extruded to obtain 3 #, 4 #, 5 # and 6 # catalysts of 20-40 mesh, respectively.

1.3 Molding of Hydrogen Type MOR Silica-Alumina Molecular Sieve 80 g Na-MOR molecular sieve with a atomic ratio of silicon to aluminum of 6.5, 28 g pseudo-boehmite and 10% dilute nitric acid were mixed homogeneously and extruded for molding, then calcined at 550° C. for 4 hours, exchanged with 0.5 mol/L ammonium nitrate for three times (2 hours for each time), washed with deionized water, dried, and calcined at 550° C. for 4 hours to obtain 7 # catalyst.

80 g Na-MOR molecular sieve with a atomic ratio of silicon to aluminum of 6.5, 20 g pseudo-boehmite and 10% dilute nitric acid were mixed homogeneously and extruded for molding, then calcined at 550° C. for 4 hours, exchanged with 0.5 mol/L ammonium nitrate for three times (2 hours for each time), washed with deionized water, dried, and calcined at 550° C. for 4 hours to obtain 8 # catalyst.

80 g Na-MOR molecular sieve with a atomic ratio of silicon to aluminum of 6.5, 50 g pseudo-boehmite and 10% dilute nitric acid were mixed homogeneously and extruded for molding, then calcined at 550° C. for 4 hours, exchanged with 0.5 mol/L ammonium nitrate for three times (2 hours for each time), washed with deionized water, dried, and calcined at 550° C. for 4 hours to obtain 9 # catalyst.

1.4 Loaded Type M/ZSM-5 Catalyst

The loaded type M/ZSM-5 catalysts were prepared by the equal volume impregnation method. 2.02 g of $KNO_3$, 3.24 g of $Cs_2CO_3$ and 1.88 g of $Cu(NO_3)_2$ were each dissolved in 18 ml of deionized water to prepare the corresponding aqueous nitrate solutions. 20 g of 6 # catalyst was added to each of the above salt solutions, stood for 24 hours, then separated, and washed with deionized water. The obtained samples were dried in an oven at 120° C. for 12 hours. The dried samples were placed in a muffle furnace, heated to a treatment temperature of 550° C. with a heating rate of 2° C./min and calcined for 4 h to obtain 10 #, 11 # and 12 # catalysts, respectively.

2 Synthesis Example

2.1 Aldol Condensation Reaction on Different Molecular Sieves

1 # to 12 # acidic molecular sieves with different topologies were pressed under a pressure of 40 MPa, and particles of 20-40 mesh were screened for testing. The molecular sieve catalyst was packed in a fixed bed reactor, and the catalyst was preactivated under the following conditions: the $N_2$ flow rate was 30 ml/min, and the temperature was raised to 500° C. at a heating rate of 2° C./min and kept at 500° C. for 1 hour. Then the temperature was lowered to the desired reaction temperature of 350° C. at a nitrogen atmosphere, the pressure of the reaction system was raised to 3 MPa with nitrogen, the molar ratio of dimethoxymethane to methyl acetate was 2/1, and the total mass space velocity of raw materials was 0.3 $h^{-1}$. The results of the aldol condensation reaction under these conditions are shown in Table 1.

TABLE 1

Evaluation results of catalysts for aldol condensation reaction of methyl acetate and dimethoxymethane

| Catalyst | The conversion rate of methyl acetate (%) | The conversion rate of dimethoxymethane (%) | The selectivity of acrylic acid and its esters (%) |
|---|---|---|---|
| 1# | 19.8 | 99.4 | 0.6 |
| 2# | 26.4 | 100.0 | 0.3 |
| 3# | 51.8 | 100.0 | 1.0 |
| 4# | 17.7 | 65.4 | 4.0 |
| 5# | 53.6 | 100.0 | 3.7 |
| 6# | 28.0 | 95.1 | 43.5 |
| 7# | 16.6 | 72.3 | 6.2 |
| 8# | 25.4 | 67.2 | 8.6 |
| 9# | 13.2 | 58.7 | 6.7 |
| 10# | 38.8 | 100.0 | 20.1 |
| 11# | 57.6 | 100.0 | 30.8 |
| 12# | 40.6 | 95.7 | 12.4 |

2.2 Aldol Condensation Reaction Results at Different Reaction Temperatures 0.5 g of 6 # catalyst was added into a fixed-bed reactor with an inner diameter of 8 mm, and the temperature was raised to 500° C. at a heating rate of 2° C./min under nitrogen atmosphere and was kept at 500° C. for 1 hour. Then the temperature was lowered to the desired reaction temperature under nitrogen atmosphere, and the pressure of the reaction system was raised to 3 MPa with nitrogen. The reaction raw materials were introduced into the reactor from top to bottom. The molar ratio of dimethoxymethane to methyl acetate was 2/1, and the total mass space velocity of raw materials was $0.3 h^{-1}$. The results of aldol condensation reaction at different reaction temperatures are shown in Table 2.

TABLE 2

Evaluation results of aldol condensation reaction at different reaction temperatures

| Reaction temperature/ ° C. | The conversion rate of methyl acetate (%) | The conversion rate of dimethoxymethane (%) | The selectivity of acrylic acid and its esters (%) |
|---|---|---|---|
| 230 | 23.4 | 100.0 | 0.0 |
| 260 | 11.7 | 96.3 | 0.0 |
| 290 | 12.8 | 96.3 | 9.7 |
| 320 | 16.4 | 96.0 | 29.4 |
| 350 | 28.0 | 95.1 | 43.5 |
| 380 | 34.9 | 94.0 | 54.7 |
| 410 | 40.2 | 92.7 | 51.3 |

2.3 Aldol Condensation Reaction Results Under Different Reaction Pressures 0.5 g of 6 # catalyst was added into a fixed-bed reactor with an inner diameter of 8 mm, and the temperature was raised to 500° C. at a heating rate of 2° C./min under nitrogen atmosphere and was kept at 500° C. for 1 hour. Then the temperature was lowered to 350° C. under nitrogen atmosphere, and the pressure of the reaction system was raised to the pressure required for the reaction with nitrogen. The reaction raw materials were introduced into the reactor from top to bottom. The molar ratio of dimethoxymethane to methyl acetate was 2/1, and the total mass space velocity of raw materials was $0.3 h^{-1}$. The results of aldol condensation reaction at different reaction pressures are shown in Table 3.

TABLE 3

Results of aldol condensation reaction on acidic molecular sieves at different reaction pressures

| Reaction pressure (MPa) | 0.2 | 3 | 5 |
|---|---|---|---|
| The conversion rate of dimethoxymethane (%) | 100.0 | 95.1 | 90.2 |
| The conversion rate of methyl acetate (%) | 12.5 | 28.0 | 31.2 |
| The selectivity of acrylic acid and methyl acrylate (%) | 9.4 | 43.5 | 47.5 |

2.4 Aldol Condensation Reaction Results at Different Molar Ratios of Dimethoxymethane to Methyl Acetate 0.5 g of 6 # catalyst was added into a fixed-bed reactor with an inner diameter of 8 mm, and the temperature was raised to 500° C. at a heating rate of 2° C./min under nitrogen atmosphere and was kept at 500° C. for 1 hour. Then the temperature was lowered to 350° C. under nitrogen atmosphere, and the pressure of the reaction system was raised to the pressure of 3 MPa required for the reaction with nitrogen. The reaction raw materials were introduced into the reactor from top to bottom. The total mass space velocity of raw materials was $0.3 h^{-1}$. The molar ratios of dimethoxymethane to methyl acetate were 2/1, 1/1 and 1/10, and the results of the aldol condensation reaction are shown in Table 4.

TABLE 4

Results of aldol condensation reaction at different molar ratios of dimethoxymethane to methyl acetate

| | The molar ratio of dimethoxymethane to methyl acetate | | |
|---|---|---|---|
| | 2/1 | 1/1 | 1/10 |
| The conversion rate of dimethoxymethane (%) | 95.1 | 98.4 | 100.0 |
| The conversion rate of methyl acetate (%) | 28.0 | 20.3 | 18.7 |
| The selectivity of acrylic acid and methyl acrylate (%) | 43.5 | 50.9 | 38.6 |

2.5 Aldol Condensation Reaction Results Under Dimethoxymethane with Different Fatty Acid Esters on Acidic Molecular Sieves 0.5 g of 6 # catalyst was added into a fixed-bed reactor with an inner diameter of 8 mm, and the temperature was raised to 500° C. at a heating rate of 2° C./min under nitrogen atmosphere and was kept at 500° C. for 1 hour. Then the temperature was lowered to 350° C. under nitrogen atmosphere, and the pressure of the reaction system was raised to the pressure of 3 MPa required for the reaction with nitrogen. The reaction raw materials were introduced into the reactor from top to bottom. The total mass space velocity of raw materials was $0.3 h^{-1}$, and the molar ratio of dimethoxymethane to different fatty acid esters was 2/1. The results of aldol condensation reaction are shown in Table 5.

TABLE 5

Results of aldol condensation reaction under dimethoxymethane with different fatty acid esters on acidic molecular sieves

| $R_1$ | $R_2$ | The conversion rate of fatty acid ester (%) | The conversion rate of dimethoxymethane (%) | The selectivity of unsaturated fatty acid ester (%) |
|---|---|---|---|---|
| H— | $CH_3$— | 28.0 | 95.1 | 43.5 |
| H— | H— | 35.7 | 99.5 | 51.3 |
| $CH_3$— | H— | 15.6 | 90.1 | 31.2 |

2.6 Aldol Condensation Reaction Results Under Different Mass Space Velocities of Raw Materials 6 # catalyst was used, the reaction temperature was 350° C., the total mass space velocities of raw materials were $0.3 h^{-1}$, $1.0 h^{-1}$ and $2.0 h^{-1}$, and the other conditions were the same as those in Example 2.1. The reaction results are shown in Table 6.

TABLE 6

Results of aldol condensation reaction under different mass space velocities of raw materials

| | The total mass space velocity of raw materials (h$^{-1}$) | | |
|---|---|---|---|
| | 0.3 | 1.0 | 2.0 |
| The conversion rate of dimethoxymethane (%) | 95.1 | 98.4 | 100.0 |
| The conversion rate of methyl acetate (%) | 28.0 | 40.1 | 56.3 |
| The selectivity of acrylic acid and methyl acrylate (%) | 43.5 | 50.9 | 38.6 |

2.7 Reaction Results Under Different Reactor Types

7 # catalyst was used, the reaction temperature was 350° C., the reactors were a fluidized bed reactor and a moving bed reactor respectively, and the other conditions were the same as those in Example 2.1. The reaction results are shown in Table 7.

TABLE 7

Results of aldol condensation reaction on acidic molecular sieves under different reactor types

| Reactor type | Fixed bed | Moving bed |
|---|---|---|
| The conversion rate of dimethoxymethane (%) | 72.3 | 80.1 |
| The conversion rate of methyl acetate (%) | 16.6 | 11.2 |
| The selectivity of acrylic acid and methyl acrylate (%) | 6.2 | 8.9 |

2.8 Reaction Results Under Different Reaction Atmospheres

10 # catalyst was used, the reaction temperature was 350° C., the reaction atmospheres were $N_2$, $H_2$, He and CO, respectively, and the other conditions were the same as those in Example 2.1. The reaction results are shown in Table 8.

TABLE 8

Results of aldol condensation reaction on acidic molecular sieves under different reaction atmospheres

| Reaction atmosphere | $N_2$ | $H_2$ | He | CO |
|---|---|---|---|---|
| The conversion rate of dimethoxymethane (%) | 100.0 | 100.0 | 100.0 | 100.0 |
| The conversion rate of methyl acetate (%) | 38.8 | 58.6 | 35.6 | 12.5 |
| The selectivity of acrylic acid and methyl acrylate (%) | 30.8 | 10.9 | 29.7 | 6.8 |

The present invention has been described in detail as above. However, the present invention is not limited to the specific embodiments as mentioned herein. It will be understood that any other variations and modifications may be made by those skilled in the art without departing from the scope of the present invention. The scopes of the present invention are limited by the claims as appended.

What is claimed is:

1. A method for preparing a lower unsaturated fatty acid or ester, comprising carrying out an aldol condensation reaction between dimethoxymethane and an acid or ester with a molecular formula of $R_1$—$CH_2COOR_2$ in a reactor loaded with an acidic molecular sieve catalyst to obtain the corresponding lower unsaturated fatty acid or ester, wherein $R_1$ and $R_2$ are each independently selected from H—, $CH_3$—, $CH_3CH$—, $CH_3(CH_2)_2$— and $CH_3(CH_2)_3$—;

wherein the acidic molecular sieve catalyst is selected from the group consisting of a SAPO-34 molecular sieve, a DNL-6 molecular sieve, a ZSM-35 molecular sieve, a ZSM-5 molecular sieve, a MOR molecular sieve, a Y molecular sieve, a βeta molecular sieve, a MCM-22 molecular sieve and a combination thereof; and the aldol condensation reaction takes place in a moving bed reactor.

2. The method according to claim 1, wherein $R_1$ and $R_2$ are each selected from H— and $CH_3$—.

3. The method according to claim 1, wherein the acidic molecular sieve catalyst is selected from the group consisting of a silica-alumina molecular sieve, an aluminum phosphate molecular sieve and combinations thereof.

4. The method according to claim 3, wherein the silica-alumina molecular sieve in the acidic molecular sieve catalyst has an atomic ratio of silicon to aluminum in a range of 1~50:1.

5. The method according to claim 3, wherein the silica-alumina molecular sieve in the acidic molecular sieve catalyst has an atomic ratio of silicon to aluminum in a range of 2~25:1.

6. The method according to claim 3, wherein the acidic molecular sieve catalyst is further modified by a metal element other than the framework constituent elements of the molecular sieve.

7. The method according to claim 6, wherein the metal element is selected from the group consisting of potassium, cesium, copper and combinations thereof.

8. The method according to claim 7, wherein the metal element is introduced into the acidic molecular sieve catalyst by in-situ synthesis, metal ion exchange or impregnation.

9. The method according to claim 8, wherein the weight percentage of the metal element calculated by metal elementary substance is in a range from 0.01 wt % to 10.0 wt %, based on the total weight of the acidic molecular sieve catalyst.

10. The method according to claim 1, wherein the acidic molecular sieve catalyst comprises a binder selected from the group consisting of alumina, silica, zirconia, magnesia and combinations thereof.

11. The method according to claim 10, wherein the content of the binder is in a range from 0 wt % to 50 wt % excluding 0 wt %, based on the total weight of the acidic molecular sieve catalyst.

12. The method according to claim 1, wherein the molar ratio of dimethoxymethane to the acid or ester is in a range from 1/20 to 5/1; the total mass space velocity of raw materials in the aldol condensation reaction is in a range from 0.05 h$^{-1}$ to 10.0 h$^{-1}$; the reaction temperature is in a range from 200° C. to 400° C.; and the reaction pressure is in a range from 0.2 MPa to 15.0 MPa.

13. The method according to claim 12, wherein the molar ratio of dimethoxymethane to the acid or ester is in a range from 1/10 to 2/1; the total mass space velocity of raw materials in the aldol condensation reaction is in a range from 0.3 h$^{-1}$ to 2.0 h$^{-1}$; the reaction temperature is in a range from 250° C. to 350° C.; and the reaction pressure is in a range from 0.2 MPa to 5.0 MPa.

14. The method according to claim 1, wherein the aldol condensation reaction is carried out in an atmosphere comprising a gas selected from the group consisting of $N_2$, He, Ar, $CH_4$, $C_2H_6$, $H_2$, CO, $CO_2$ and combinations thereof.

15. The method according to claim 3, wherein the acidic molecular sieve catalyst comprises a binder selected from the group consisting of alumina, silica, zirconia, magnesia and combinations thereof.

16. The method according to claim 9, wherein the acidic molecular sieve catalyst comprises a binder selected from the group consisting of alumina, silica, zirconia, magnesia and combinations thereof.

* * * * *